US012586324B2

(12) United States Patent
Fleig et al.

(10) Patent No.: US 12,586,324 B2
(45) Date of Patent: Mar. 24, 2026

(54) SPINE LEVEL DETERMINATION USING AUGMENTED REALITY

(71) Applicant: Brainlab SE, Munich (DE)

(72) Inventors: Oliver Fleig, Baldham (DE); Martin Koestler, Munich (DE); Christian Schmaler, Munich (DE); Christian Dax, Munich (DE); Nicole Kerstein, Munich (DE); Juliane Weinzierl, Munich (DE)

(73) Assignee: Brainlab SE, Munich (DE)

( * ) Notice: Subject to any disclaimer, the term of this patent is extended or adjusted under 35 U.S.C. 154(b) by 63 days.

(21) Appl. No.: 18/579,772

(22) PCT Filed: Dec. 21, 2022

(86) PCT No.: PCT/EP2022/087360
§ 371 (c)(1),
(2) Date: Jan. 16, 2024

(87) PCT Pub. No.: WO2024/132140
PCT Pub. Date: Jun. 27, 2024

(65) Prior Publication Data
US 2025/0078419 A1      Mar. 6, 2025

(51) Int. Cl.
*G06T 19/00* (2011.01)
*G02B 27/01* (2006.01)
*G16H 30/40* (2018.01)

(52) U.S. Cl.
CPC ........ *G06T 19/006* (2013.01); *G02B 27/0172* (2013.01); *G16H 30/40* (2018.01); *G06T 2219/2004* (2013.01)

(58) Field of Classification Search
CPC ........... G06T 19/006; G06T 2219/2004; G06F 3/011; G02B 27/0172; G16H 30/40
See application file for complete search history.

(56) References Cited

U.S. PATENT DOCUMENTS

| | | | |
|---|---|---|---|
| 10,010,379 B1 | 7/2018 | Gibby | |
| 10,497,469 B2 | 12/2019 | Popescu | |

(Continued)

FOREIGN PATENT DOCUMENTS

| | | |
|---|---|---|
| EP | 3593227 A1 | 1/2020 |
| WO | 2022161626 A1 | 8/2022 |

OTHER PUBLICATIONS

Rong Huang, Angelika Maag, and Moshiur Bhuiyan, Augmented Reality Navigation in Spine Surgery, 2020 5th International Conference on Innovative Technologies in Intelligent Systems and Industrial Applications (CITISIA), Sydney, Australia, 2020, pp. 1-10. (Year: 2020).*

(Continued)

*Primary Examiner* — Jeffery A Brier
(74) *Attorney, Agent, or Firm* — Gray Ice Higdon

(57) ABSTRACT

Disclosed is a computer-implemented method of registering a digital model of an anatomical body part corresponding to a patient body part. The method encompasses input, to an augmented reality viewing device, of data defining a digital model of an anatomical body part. The model comprises at least one vertex which corresponds to a specific part of the anatomical body part. The specific part is, for example, a landmark easily identifiable for a user, such as a specific vertebra which may be found by palpation. Based on a known orientation of the augmented reality viewing device relative to the anatomical body part, visual information is displayed on a viewing unit of the augmented reality viewing device. The visual information indicates the position of the vertex as an overlay on the position of the specific part of the anatomical body part in the field of view of the augmented reality viewing device.

17 Claims, 4 Drawing Sheets

(56)         References Cited

U.S. PATENT DOCUMENTS

| | | | |
|---|---|---|---|
| 11,166,764 B2 * | 11/2021 | Roh ...................... | A61B 90/37 |
| 2016/0191887 A1 | 6/2016 | Casas | |
| 2022/0265363 A1 | 8/2022 | Uhde | |

OTHER PUBLICATIONS

International Searching Authority, International Search Report and the Written Opinion issued in Application No. PCT/EP2022/087360, 13 pages, dated Jun. 26, 2023.

* cited by examiner

4

SPINE LEVEL DETERMINATION USING AUGMENTED REALITY

FIELD OF THE INVENTION

The present invention relates to a computer-implemented method of registering a digital model of an anatomical body part corresponding to a patient body part, a corresponding computer program, a computer-readable storage medium storing such a program and a computer executing the program, as well as a medical system comprising an electronic data storage device and the aforementioned computer.

TECHNICAL BACKGROUND

In spine surgery an important task is finding the correct position (e.g. the correct vertebra) for the incision. The vertebrae are numbered, the numbers are referred to as level. The radiologists note the correct level in their report for the scan. Often they can deduce the level from the scout view of the patient. The scout view is a large 2D low resolution scan (sagittal or coronal most of the time), which covers a large area to determine the region of interest for the subsequent diagnostic scan. However, it is difficult to find the correct level with the necessary certainty. Surgeons frequently count the spinous processes. On obese patients this is often not possible. Surgeons then place an instrument or a radiopaque marker at the assumed position of the correct vertebra and take an x-ray image for verification. Sometimes several such images are necessary to find the correct location.

The invention allows to minimize or totally avoid the acquisition of additional x-ray images and minimize exposure to radiation during surgery. Handling a C-arm for the image acquisition is cumbersome.

The present invention has the object of providing an improved method of determining the position of anatomical landmarks on a patient.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The disclosed method encompasses input, to an augmented reality viewing device, of data defining a digital model of an anatomical body part, for example of the spine. The model comprises at least one vertex which corresponds to a specific part of the anatomical body part. The specific part is for example a landmark which is easily identifiable for a user, such as a specific vertebra which may be found by palpation.

Based on a known orientation of the augmented reality viewing device relative to the anatomical body part, visual information is displayed on a viewing unit of the augmented reality viewing device. The visual information indicates the position of the vertex as an overlay on the position of the specific part of the anatomical body part in the field of view of the augmented reality viewing device.

GENERAL DESCRIPTION OF THE INVENTION

In this section, a description of the general features of the present invention is given for example by referring to possible embodiments of the invention.

In general, the invention reaches the aforementioned object by providing, in a first aspect, a computer-implemented medical method of registering a digital model of an anatomical body part corresponding to a patient body part, for example registering the digital model with a positional display reference system of an augmented reality viewing device in which positions of image information to be displayed by the augmented reality viewing device are defined. The method comprises executing, on at least one processor of at least one computer (for example at least one computer being part of a navigation system), the following exemplary steps which are executed by the at least one processor.

In a (for example first) exemplary step, body part model data is acquired which describes the digital model which comprises at least one vertex corresponding to a predetermined element of the patient body part. For example, the patient body part comprises or consists of the spine. For example, the digital model comprises a plurality of vertices having a fixed scaling of positions relative to one another for example in a plurality of degrees of freedom. The digital model can therefore be termed a string of pearls model in which pearls representing the vertices of the model can move relative to one another within the degrees of freedom provided by a string joining each two pearls, for example under the boundary condition that one degree of freedom is fixed (such that e.g. all pearls are on fixed coordinate in one spatial direction, i.e. on one straight line in the spatial direction). For example, the digital model comprises a plurality of vertices, wherein all vertices of the digital model lie on a single straight line in one degree of freedom. For example, the digital model has been generated from at least one of atlas data describing a synthesized model of the anatomical body part and patient medical image data describing the patient body part. The patient medical image data may be a digital planning image generated for example by computed x-ray tomography, magnetic resonance tomography or radiography.

In a (for example second) exemplary step, viewing device position data is acquired which describes a relative position between a head-mountable, for example head-mounted, augmented reality (including mixed reality such as augmented reality) viewing device and at least one position, for example at least two positions or one position and a vector having a scaling and a direction or a default value, in a reference system used to generate an augmented reality image with the augmented reality viewing device. For example, the augmented reality device is a mixed reality device.

In a (for example third) exemplary step, augmented reality display data is determined based on the body part model data and the viewing device position data, wherein the augmented reality display data describes an image rendering of the digital model to be displayed on a viewing unit of the augmented reality viewing device and the position at which the image rendering of the digital model is to be displayed relative to a field of view of the viewing unit so that an image rendering of the position, in the digital model, of the at least one vertex corresponding to the predetermined element is displayed on the viewing unit as an overlay, i.e. injected image, on the position of the predetermined element. The at least one vertex is for example a landmark (an anatomical landmark) which is easily identifiable for a user, such a specific vertebra which may be found by palpation. For example, the digital model comprises at least two vertices each corresponding to a different predetermined element of the patient body part. For example, the augmented reality display data describes the position at which the image rendering of the digital model is to be displayed relative to the field of view of the viewing unit so that image renderings of the positions, in the digital model, of the at least two vertices corresponding to the predetermined elements are displayed on the viewing unit as overlays on the positions of the respectively corresponding predetermined elements. For example, the position of the image rendering of the position of the at least one vertex is defined in a display reference system and the position of a projection of the predetermined element into the display reference system coincides with the position of the image rendering of the position of the at least one vertex, for example coincides with the position of the image rendering of the position of the at least one vertex also if the viewing device moves relative to the patient body part. For example, the viewing device position data describes a current field of view of the viewing device defined in the display reference system and the image rendering of the at least one vertex is displayed on the viewing unit as an overlay on the position of the predetermined element only if the predetermined element lies in the field of view. For example, the viewing device position data is determined by tracking the augmented reality viewing device for example using optical navigation, for example an imaging device mounted on the augmented reality viewing device. The term "tracking" refers to tracking the position of the augmented reality viewing device.

In an example of the method according to the first aspect, pointer position data is acquired which describes the position of a pointer relative to the field of view and determining the position at which the image rendering is to be displayed relative to the field of view based on the pointer position data. The pointer is for example an instrument (a pointing instrument) or a (human) finger or another type of position indicating device such as a marker device, the marker device being placed at the respective position. Such a marker comprises for example a plurality of markers placed at a respective plurality of positions, or comprises an orientable feature (which is for example rotationally asymmetric in two or three dimensions) for determining the orientation of the patient body part and a corresponding orientation of the digital model. For example, the pointer position data describes one position of the pointer and a direction in the reference system used to generate an augmented reality image or two positions of the pointer in the reference system used to generate an augmented reality image, and wherein for example determining the position at which the image rendering is to be displayed includes a deformation of the digital model or a translation of the digital model, for example a stretching of the string of pearls model which means an increase in the length of string available between each two pearls. For example, the pointer position data describes a plurality of positions of the pointer device which have been acquired in a predetermined order. For example, the position of the pointer describes the position of an element of the patient body part corresponding to a vertex of the digital model.

In a further exemplary step of the method according to the first aspect, an indication is displayed on the viewing unit which describes the at least one vertex, for example the position of the at least one vertex in the reference system used to generate an augmented reality image.

In a second aspect, the invention is directed to a computer program comprising instructions which, when the program is executed by at least one computer, causes the at least one computer to carry out method according to the first aspect. The invention may alternatively or additionally relate to a (physical, for example electrical, for example technically generated) signal wave, for example a digital signal wave, such as an electromagnetic carrier wave carrying information which represents the program, for example the aforementioned program, which for example comprises code means which are adapted to perform any or all of the steps of the method according to the first aspect. The signal wave is in one example a data carrier signal carrying the aforementioned computer program. A computer program stored on a disc is a data file, and when the file is read out and transmitted it becomes a data stream for example in the form of a (physical, for example electrical, for example technically generated) signal. The signal can be implemented as the signal wave, for example as the electromagnetic carrier wave which is described herein. For example, the signal, for example the signal wave is constituted to be transmitted via a computer network, for example LAN, WLAN, WAN, mobile network, for example the internet. For example, the signal, for example the signal wave, is constituted to be transmitted by optic or acoustic data transmission. The invention according to the second aspect therefore may alternatively or additionally relate to a data stream representative of the aforementioned program, i.e. comprising the program.

In a third aspect, the invention is directed to a computer-readable storage medium on which the program according to the second aspect is stored. The program storage medium is for example non-transitory.

In a fourth aspect, the invention is directed to at least one computer (for example, a computer), comprising at least one processor (for example, a processor), wherein the program according to the second aspect is executed by the processor, or wherein the at least one computer comprises the computer-readable storage medium according to the third aspect.

In a fifth aspect, the invention is directed to a medical system, comprising:

a) the at least one computer according to the preceding claim;

b) at least one electronic data storage device storing at least the body part model data;

c) a head-mountable augmented reality viewing device; and d) a navigation device for detecting the position of the viewing device and for example the patient body part, wherein for example the navigation device is part of the augmented reality viewing device, and wherein the at least one computer is operably coupled to the at least one electronic data storage device for acquiring, from the at least one data storage device, at least the body part model data, and the navigation device for receiving, from the navigation device, an electronic signal corresponding to the viewing device position data, and the viewing device for transmitting, to the viewing device, electronic signals corresponding to the augmented reality display data.

Alternatively or additionally, the invention according to the fifth aspect is directed to a for example non-transitory computer-readable program storage medium storing a program for causing the computer according to the fourth aspect to execute the data processing steps of the method according to the first aspect.

For example, the disclosed method is not a method for treatment of the human or animal body by surgery or therapy. For example, the invention does not involve or in particular comprise or encompass an invasive step which would represent a substantial physical interference with the body requiring professional medical expertise to be carried out and entailing a substantial health risk even when carried out with the required professional care and expertise.

More particularly, the invention does not involve or in particular comprise or encompass any surgical or therapeutic activity. No surgical or therapeutic activity and in particular no surgical or therapeutic step is necessitated or implied by carrying out the invention.

The present invention also relates to the use of the system according to the fifth aspect for example for determining the position of the patient body part.

Definitions

In this section, definitions for specific terminology used in this disclosure are offered which also form part of the present disclosure.

The method in accordance with the invention is for example a computer-implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term computer includes a server resource. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a computer program comprising instructions which, when on the program is executed by a computer, cause the computer to carry out the method or methods, for example, the steps of the method or methods, described herein and/or to a computer-readable storage medium (for example, a non-transitory computer-readable storage medium) on which the program is stored and/or to a computer comprising said program storage medium and/or to a (physical, for example electrical, for example technically generated) signal wave, for example a digital signal wave, such as an electromagnetic carrier wave carrying information which represents the program, for example the aforementioned program, which for example comprises code means which are adapted to perform any or all of the method steps described herein. The signal wave is in one example a data carrier signal carrying the aforementioned computer program. The invention also relates to a computer comprising at least one processor and/or the aforementioned computer-readable storage medium and for example a memory, wherein the program is executed by the processor.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination.

Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Image registration is the process of transforming different sets of data into one coordinate system. The data can be multiple photographs and/or data from different sensors, different times or different viewpoints. It is used in computer vision, medical imaging and in compiling and analysing images and data from satellites. Registration is necessary in order to be able to compare or integrate the data obtained from these different measurements.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows determining the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

A pointer is a rod which comprises one or more-advantageously, two-markers fastened to it and which can be used to measure off individual co-ordinates, for example spatial co-ordinates (i.e. three-dimensional co-ordinates), on a part of the body, wherein a user guides the pointer (for example, a part of the pointer which has a defined and advantageously fixed position with respect to the at least one marker attached to the pointer) to the position corresponding to the co-ordinates, such that the position of the pointer can be determined by using a surgical navigation system to detect the marker on the pointer. The relative location between the markers of the pointer and the part of the pointer used to measure off co-ordinates (for example, the tip of the pointer) is for example known. The surgical navigation system then enables the location (of the three-dimensional co-ordinates) to be assigned to a predetermined body structure, wherein the assignment can be made automatically or by user intervention.

A landmark is a defined element of an anatomical body part which is always identical or recurs with a high degree of similarity in the same anatomical body part of multiple patients. Typical landmarks are for example the epicondyles of a femoral bone or the tips of the transverse processes and/or dorsal process of a vertebra. The points (main points or auxiliary points) can represent such landmarks. A landmark which lies on (for example on the surface of) a characteristic anatomical structure of the body part can also represent said structure. The landmark can represent the anatomical structure as a whole or only a point or part of it. A landmark can also for example lie on the anatomical structure, which is for example a prominent structure. An example of such an anatomical structure is the posterior aspect of the iliac crest. Another example of a landmark is one defined by the rim of the acetabulum, for instance by the centre of said rim. In another example, a landmark represents the bottom or deepest point of an acetabulum, which is derived from a multitude of detection points. Thus, one landmark can for example represent a multitude of detection points. As mentioned above, a landmark can represent an anatomical characteristic which is defined on the basis of a characteristic structure of the body part. Additionally, a landmark can also represent an anatomical characteristic defined by a relative movement of two body parts, such as the rotational centre of the femur when moved relative to the acetabulum.

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises image information (for example, positional image information) which can be matched (for example by applying an elastic or rigid image fusion algorithm) for example to image information (for example, positional image information) contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

For example, the atlas data includes information of the anatomical body part. This information is for example at least one of patient-specific, non-patient-specific, indication-specific or non-indication-specific. The atlas data therefore describes for example at least one of a patient-specific, non-patient-specific, indication-specific or non-indication-specific atlas. For example, the atlas data includes movement information indicating a degree of freedom of movement of the anatomical body part with respect to a given reference (e.g. another anatomical body part). For example, the atlas is a multimodal atlas which defines atlas information for a plurality of (i.e. at least two) imaging modalities and contains a mapping between the atlas information in different imaging modalities (for example, a mapping between all of the modalities) so that the atlas can be used for transforming medical image information from its image depiction in a first imaging modality into its image depiction in a second imaging modality which is different from the first imaging modality or to compare (for example, match or register) images of different imaging modality with one another.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia.

The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
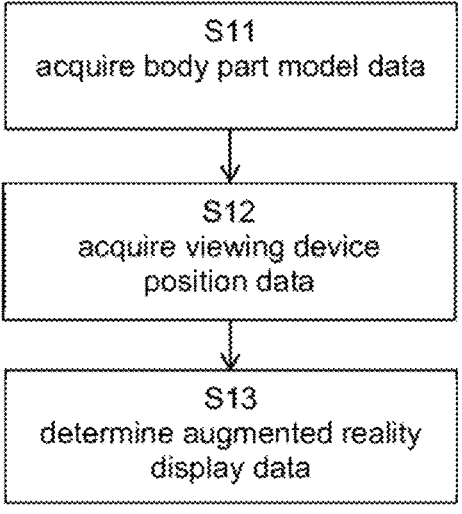
FIG. 1 illustrates the basic steps of the method according to the first aspect.

FIG. 1 illustrates the basic steps of the method according to the first aspect, in which step S11 encompasses acquisition of the body part model data, step S12 encompasses acquisition of the viewing device position data and subsequent step S13 encompasses determination of the augmented reality display data.

Figure 2:
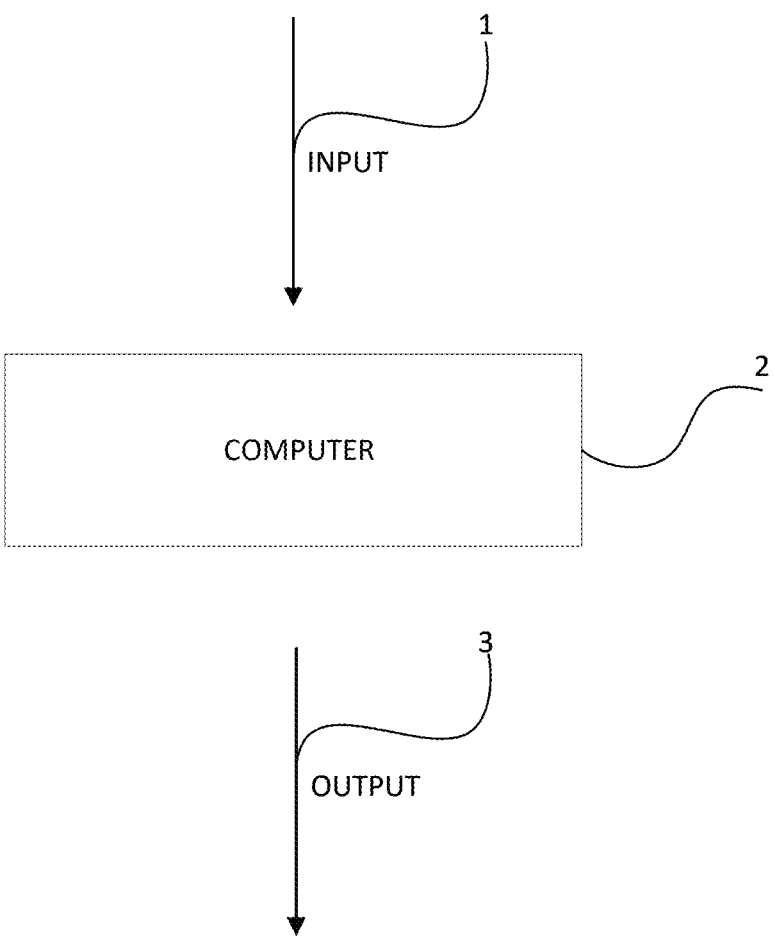
FIG. 2 shows an embodiment of the present invention, specifically the method according to the first aspect.

FIG. 2 illustrates an embodiment of the present invention that includes all essential features of the invention. In this embodiment, the entire data processing which is part of the method according to the first aspect is performed by a computer 2. Reference sign 1 denotes the input of data acquired by the method according to the first aspect into the computer 2 and reference sign 3 denotes the output of data determined by the method according to the first aspect.

Figure 3:
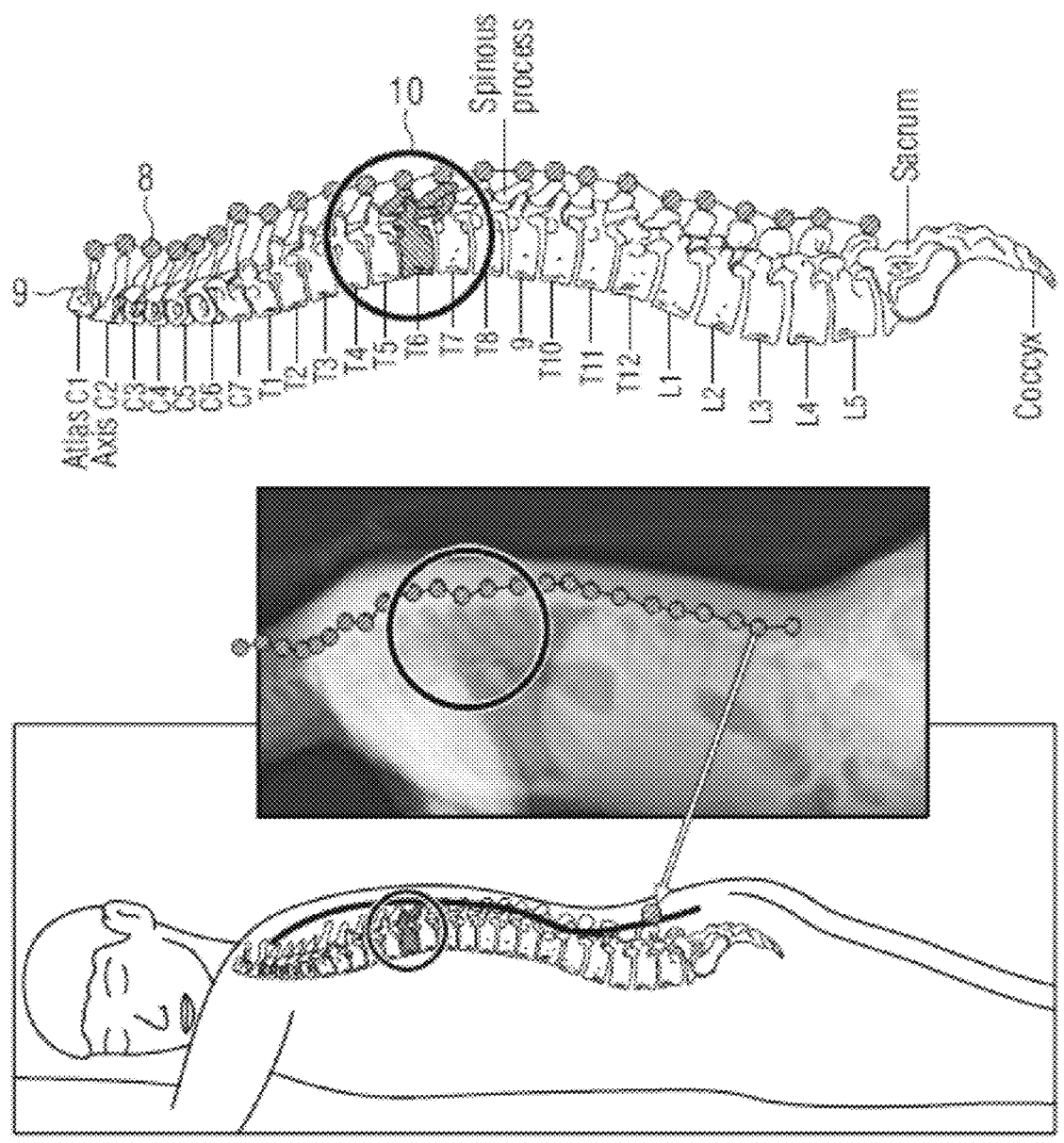
FIG. 3 is an illustration of a practical application of the method according to the first aspect.

FIG. 3 shows an environment in which the method according to the first aspect can be used. First of all, a real patient is present. An augmented reality system with overlaying graphics onto the real world (fixed in space) worn by a medical professional with optical see-through or video see-through functionality. A template is generated, i.e. bio-mechanical model is constructed with defined rules for user interactions for identifying a landmark vertebra 10. A three-dimensional string-of-pearls-model 8 of at least three pearls representing the vertebrae on the spine 9 (in one example, also with ribs) which are connected via a spring model is acquired. Additionally, a three-dimensional virtual representation of the anatomical body part of interest, e.g. the spine, is acquired. A CT scout scan can serve as a template or be used to improve the template. Anatomical structures such as vertebrae or the skin surface can be segmented on the scout scan. Optionally, a template will be selected from e.g. a drop-down list, library according to additional information, e.g. atlas data, meta data, predefined patient data (e.g. age, height, gender, disease). The distinguished point in the template may be determined as fixed points in the model or dynamically, e.g. as a selection by the user or using a 3D sensor, e.g. marker (hardware)-based. A marker will be placed on a known anatomical region of interest. The marker position and orientation are compared to planning image data. The marker is designed according to a predominant direction, e.g. spine direction. The landmark is identified using special gesture commands to determine points, e.g. a double tap or by pointer gesture commands. The real and virtual distinguished points are aligned to generate an anchor point-pair resembling the assignment of the at least one vertex to the predetermined element. Scaling can be implemented via a second point pair, via gesture, or by a handheld controller. Optionally, a distortion of the template is allowed within predefined margins. The template is adapted to a planning image. For example, the template parameter, e.g. angles, distances, spring/damping forces, etc. between the modelled links and points according to intra-operative data (point clouds) may be altered. Template-depth is determined via time-of-flight camera information. Template-orientation can be determined via tracked instruments in terms of palpating/going along the e.g. spine, levels with the tracked instruments with continuously recording triggered points. A scout scan (e.g. with an x-ray image of large field of view) can be acquired. Image data of an anatomical region of interest is acquired in the planning phase by using two-dimensional x-ray or computed x-ray tomography. The distinguished point is identified in the image data by user interaction (e.g. palpation on the basis of the provided augmented reality display data) or automatically with a tracked marker or an atlas. The planning data is then overlaid onto the view of the patient.

Figure 4:
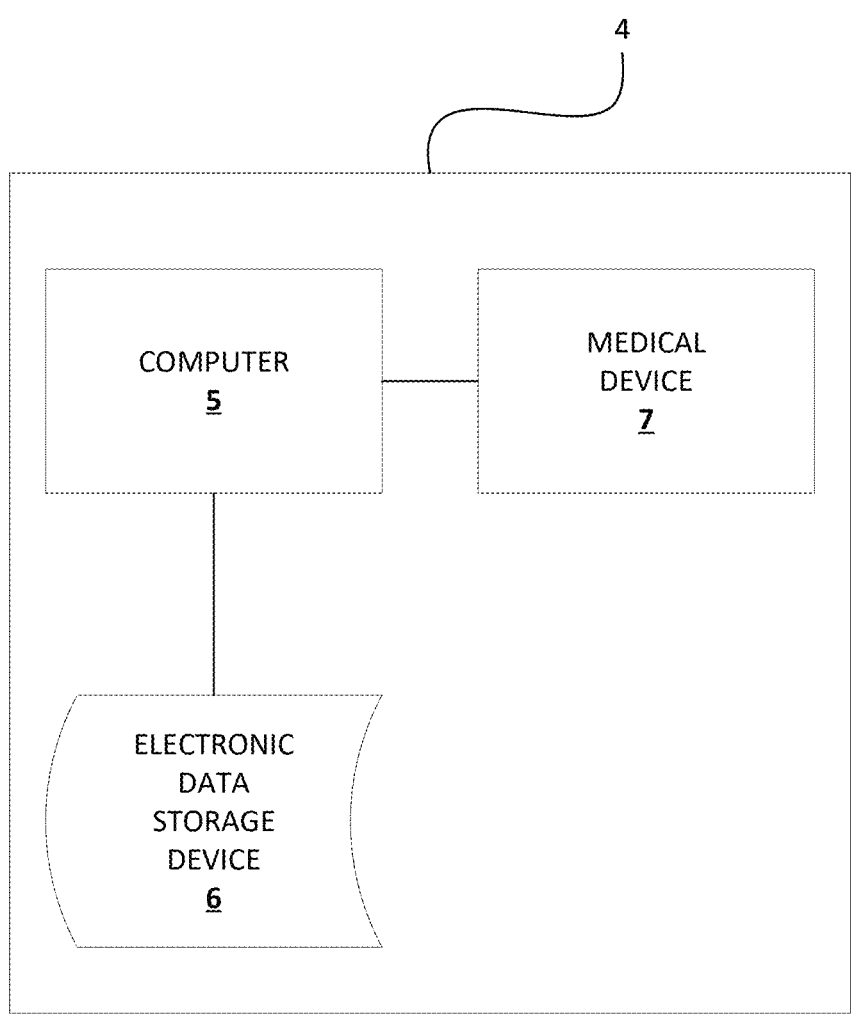
FIG. 4 is a schematic illustration of the system according to the fifth aspect.

FIG. 4 is a schematic illustration of the medical system 4 according to the fifth aspect. The system is in its entirety identified by reference sign 4 and comprises a computer 5, an electronic data storage device (such as a hard disc) 6 for storing at least the patient data and a medical device 7 (such as a navigation device or a navigation system, for example surgical navigation system). The components of the medical system 4 have the functionalities and properties explained above with regard to the fifth aspect of this disclosure.

The invention claimed is:

1. A computer-implemented method of registering a digital model of an anatomical body part corresponding to a patient body part, comprising:

acquiring body part model data which describes the digital model which comprises a plurality of vertices having a fixed scaling of positions relative to one another, wherein at least one vertex of the plurality of vertices corresponding to a predetermined element of the patient body part;

acquiring viewing device position data which describes a relative position between a head-mountable augmented reality viewing device and at least one position in a reference system used to generate an augmented reality image with the head-mountable augmented reality viewing device; and determining augmented reality display data based on the body part model data and the viewing device position data, wherein the augmented reality display data describes an image rendering of the digital model to be displayed on a viewing unit of the head-mountable augmented reality viewing device and the position at which the image rendering of the digital model is to be displayed relative to a field of view of the viewing unit so that an image rendering of the position, in the digital model, of the at least one vertex of the plurality of vertices corresponding to the predetermined element is displayed on the viewing unit as an overlay on the position of the predetermined element.

2. The method according to claim 1, wherein the digital model comprises at least two vertices each corresponding to a different predetermined element of the patient body part and wherein the augmented reality display data describes the position at which the image rendering of the digital model is to be displayed relative to the field of view of the viewing unit so that image renderings of the positions, in the digital model, of the at least two vertices corresponding to the predetermined elements are displayed on the viewing unit as overlays on the positions of the respectively corresponding predetermined elements.

3. The method according to claim 1, wherein the position of the image rendering of the position of the at least one vertex is defined in a display reference system and the position of a projection of the predetermined element into the display reference system coincides with the position of the image rendering of the position of the at least one vertex and coincides with the position of the image rendering of the position of the at least one vertex also if the viewing device moves relative to the patient body part.

4. The method according to claim 1, wherein the viewing device position data describes a current field of view of the viewing device defined in the display reference system and the image rendering of the at least one vertex is displayed on the viewing unit as an overlay on the position of the predetermined element only when the predetermined element lies in the field of view.

5. The method according to claim 1, wherein the viewing device position data is determined by tracking the head-mountable augmented reality viewing device using optical navigation.

6. The method according to claim 1, comprising
acquiring pointer position data describing the position of a pointer relative to the field of view; and
determining the position at which the image rendering is to be displayed relative to the field of view based on the pointer position data.

7. The method according to claim 6, wherein the pointer position data describes one position of the pointer and a direction in the reference system used to generate an augmented reality image or two positions of the pointer in the reference system used to generate an augmented reality image, and wherein determining the position at which the image rendering is to be displayed includes a deformation of the digital model or a translation of the digital model.

8. The method according to claim 6, wherein the pointer position data describes a plurality of positions of a pointer device which have been acquired in a predetermined order.

9. The method according to claim 6, wherein the position of the pointer describes the position of an element of the patient body part corresponding to a vertex of the digital model.

10. The method according to claim 1, further comprising displaying, on the viewing unit, an indication describing the at least one vertex, as the position of the at least one vertex in the reference system used to generate an augmented reality image.

11. The method according to claim 1, wherein the scaling of positions is fixed in a plurality of degrees of freedom.

12. The method according to claim 1, wherein the digital model comprises a plurality of vertices, wherein all vertices of the digital model lie on a single straight line in one degree of freedom.

13. The method according to claim 1, wherein the patient body part comprises a spine.

14. The method according to claim 1, wherein the augmented reality device is a mixed reality device.

15. The method according to claim 1, wherein the digital model has been generated from at least one of atlas data describing a synthesized model of the anatomical body part and patient medical image data describing the patient body part.

16. A non-transitory computer readable medium comprising instructions which, when executed by at least one processor of at least one computer, causes the at least one processor to acquire body part model data which describes a digital model which comprises a plurality of vertices having a fixed scaling of positions relative to one another, wherein at least one vertex of the plurality of vertices corresponding to a predetermined element of a patient body part;

acquire viewing device position data which describes a relative position between a head-mountable augmented reality viewing device and at least one position in a reference system used to generate an augmented reality image with the head-mountable augmented reality viewing device; and determine augmented reality display data based on the body part model data and the viewing device position data.

17. A medical system, comprising:

at least one processor operable to execute stored instructions which, when executed, cause the at least one processor to:

acquire body part model data which describes a digital model which comprises a plurality of vertices having a fixed scaling of positions relative to one another, wherein at least one vertex of the plurality of vertices corresponding to a predetermined element of a patient body part;

acquire viewing device position data which describes a relative position between a head-mountable augmented reality viewing device and at least one position in a reference system used to generate an augmented reality image with the head-mountable augmented reality viewing device; and determine augmented reality display data based on the body part model data and the viewing device position data;

at least one electronic data storage device storing at least the body part model data;

a head-mountable augmented reality viewing device; and a navigation device for detecting the position of the viewing device and for example the patient body part, wherein for example the navigation device is part of the head-mountable augmented reality viewing device, and wherein the at least one processor is operably coupled to the at least one electronic data storage device for acquiring, from the at least one data storage device, at least the body part model data; and the navigation device for receiving, from the navigation device, an electronic signal corresponding to the viewing device position data; and the viewing device for transmitting, to the viewing device, electronic signals corresponding to the augmented reality display data.

\* \* \* \* \*